United States Patent
Spohn et al.

Patent Number: 5,760,274
Date of Patent: Jun. 2, 1998

[54] METHOD OF MAKING AROMATIC NITRILES

[75] Inventors: Ronald F. Spohn, Getzville; Robert L. Bell, Amherst, both of N.Y.

[73] Assignee: Occidental Chemical Corporation, Niagara Falls, N.Y.

[21] Appl. No.: 902,482

[22] Filed: Jul. 29, 1997

[51] Int. Cl.$^6$ .................................................. C07C 253/00
[52] U.S. Cl. ........................................................ 558/329
[58] Field of Search ............................................ 558/329

[56] References Cited

FOREIGN PATENT DOCUMENTS

0441004A1  1/1991  European Pat. Off. .

OTHER PUBLICATIONS

G. Olah, Journ. of Amer. Chem. Soc., vol. 94, p. 7453 (1972).

*Primary Examiner*—Robert W. Ramsuer
*Assistant Examiner*—Joseph Murray
*Attorney, Agent, or Firm*—Richard D. Fuerle

[57] ABSTRACT

Disclosed is a method of making an aromatic nitrile by reacting a benzotrichloride having the formula

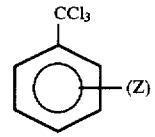

with a source of ammonia, where Z is R, X,

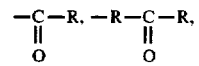

—ROR, or —OR. R is alkyl from $C_1$ to $C_{20}$ or aryl from $C_1$ to $C_{25}$, X is halogen and n is 0 to 5. The reaction is performed in the presence of 0.01 to about 5 wt % of a catalyst having the general formula $M_{p/2}O$ or $MX_p \cdot mH_2O$ and about 0.01 to about 5 wt % water, as free water or water of hydration, based on the weight of the benzotrichloride, where M is beryllium, magnesium, calcium, strontium, or barium, m is 0 to 6, and p is the valence of M.

20 Claims, No Drawings

METHOD OF MAKING AROMATIC NITRILES

BACKGROUND OF THE INVENTION

This invention relates to a method of making aromatic nitriles by the reaction of a benzotrichloride with a source of ammonia. In particular, it relates to the use of a catalyst having the formula $M_{p/2}O$ or $MX_p \cdot mH_2O$ where M is a group II-A metal, X is halogen, m is 0 to 6, and p is the valence of M.

Parachlorobenzonitrile (PCBN) and 3,4-dichlorobenzonitrile (DCBN) can be prepared by reacting parachlorobenzotrichloride (PCBTC) or 3,4-dichlorobenzotrichloride (DCBTC), respectively, with ammonium chloride and a catalyst such as ferric chloride, titanium tetrachloride, molybdenum pentachloride, antimony pentachloride, or ferrous chloride. A major problem with this reaction is the production of a trimer by-product believed to have the formula

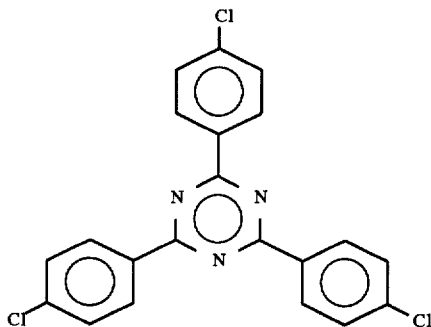

The trimer has little or no commercial value at the present time, constitutes a waste of the benzotrichloride starting material, and creates a separation and disposal problem. The use of cupric chloride or cupric oxide suppressed the production of the trimer when the starting benzotrichloride was DCBTC but did not eliminate the trimer when the starting benzotrichloride was PCBTC. In addition, the presence of a copper in the trimer waste created a hazardous heavy metal disposal problem. (The ortho substituted precursors, such as orthochlorobenzotrichloride (OCBTC), form very little trimer with the standard catalyst, perhaps due to steric hinderance by the ortho substituted group.)

SUMMARY OF THE INVENTION

We have discovered that oxides and halogen salts of group IIA metals, particularly magnesium chloride and magnesium oxide, will catalyze the production of the corresponding nitriles from various benzotrichlorides. It is a surprising result that magnesium chloride is an active catalyst in this reaction because it is described as being a very weak or inactive benzylation catalyst when compared to many other Friedel-Crafts Catalysts. (See Page 7458 of an article by G. Olah in the Journal of the American Chemical Society, Volume 94 (1972).) A major advantage of the method of this invention is that very little of the trimer compounds are produced.

In addition, the catalysts of this invention, particularly magnesium chloride and magnesium oxide, are inexpensive and do not constitute a hazardous heavy metal waste.

DESCRIPTION OF THE PREFERRED EMBODIMENTS

This invention is applicable to benzotrichloride having the general formula

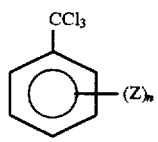

where Z is R, X,

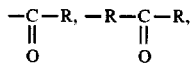

—ROR, or —OR. R is alkyl from $C_1$ to $C_{20}$ or aryl from $C_1$ to $C_{25}$. X is halogen, and n is 0 to 5. In the formula, Z is preferably halogen (X) as halogens work well in this reaction; the preferred halogen is chlorine because those compounds are the most commercially valuable. Also in the general formula, n is preferably 1 or 2 because those compounds are more commercially important. If n in the formula is 1 then Z is preferably in the para position and if n is 2 then the two Z groups are preferably in the 3,4 positions because catalysts outside the scope of this invention do not work well on 3,4-substituted benzotrichlorides in that they tend to produce a great deal of trimer.

Benzotrichloride is reacted with 1 to 3 moles of a source of ammonia per mole of the benzotrichloride. If less ammonia source is used some of the benzotrichloride will be unreacted and more ammonia source is unnecessary and may create a waste disposal problem. It is preferable to use about 1.05 to about 1.1 moles of a source of ammonia per mole of the benzotrichloride. Examples of suitable sources of ammonia include ammonia gas, urea, ammonium chloride, other ammonium halides such as ammonium bromide, ammonium iodine, or ammonium fluoride, and other ammonium organic salts such as ammonium acetate, or ammonium propionate. Ammonium chloride is preferred because it is easy to handle and ammonia gas is preferred because it is inexpensive, makes the reaction easier to control, and permits a continuous reaction. Urea is not preferred because it tends to make side products and it is more expensive.

The catalyst for the reaction has the general formula $M_{p/2}O$ or $MX_p \cdot mH_2O$, where M is beryllium, magnesium, calcium, strontium, or barium. Magnesium is preferred because it has been found to work well and is inexpensive. In the formula, X, as before, is halogen, preferably chlorine. The preferred compounds are magnesium chloride and magnesium oxide because they have been found to work very well. The amount of catalyst used should be about 0.01 to about 5 wt %, based on the weight of the benzotrichloride, as less catalyst results in a slow reaction and, while more catalyst results in a faster reaction and a lower temperature, the evolution of hydrogen chloride may be so rapid as to create a handling problem. Preferably, the amount of catalyst is about 0.1 to about 1 wt %, based on the weight of benzotrichloride.

A small amount of water, about 0.01 to about 5 wt % based on the weight of the benzotrichloride, should be present during the reaction. If less water is present, little reaction occurs and more water may result in too many side products, such as amides; the preferred amount of water is about 0.1 to about 1 wt %, based on the weight of the benzotrichloride. The water may be present as free water or as water of hydration on the catalyst, but is preferably present as free water as that tends to produce better results.

The reaction occurs at an elevated temperature up to about the boiling point of the product, although higher temperatures can be used if the reaction is under pressure. Generally, a minimum temperature of about 170° C. is required as at lower temperatures the reaction is too slow. Higher temperatures are faster but require more energy. To produce PCBN, a temperature range of about 200° to about 220° C. is preferred and to produce DCBTF, a temperature range of about 220° to about 240° C. is preferred. The reaction requires about 1 to about 40 hours to complete and completion of the reaction can be determined by monitoring the evolution of hydrogen chloride. The hydrogen chloride evolved during the reaction can be scrubbed into water or caustic or can be collected for sale or use for acidification reactions. The nitrile product can be isolated by distillation, which separates it from all the important by-products except for the acid chloride.

The following examples further illustrate this invention.

EXAMPLE 1

A 2 L glass resin kettle was fitted with an overhead stirrer, glass thermocouple well, and a 15 cm (6 inch) 24/40 U-connector tube wrapped with an electrical heating tape and set at a 120° to 150° C. skin temperature. The U-connector tube was attached to a 1 L, 3-necked, round bottom flask fitted with an air condenser, which was used as a sublimate trap to a stop the easily sublimed product. To this was added either 1.1 eq. (first two runs) or 1.0 eq. (last three runs) NH$_4$Cl, 7.50 g MgO (0.5 wt % based on the PCBTC) and 1500 g of 99 wt % PCBTC. The kettle was heated with a mantle to 220° C. The temperature was controlled using an Instruments for Research and Industry "Therm-O-Watch" model L11-1500 temperature controller with a K-type thermocouple. Samples were removed periodically and were analyzed by gas chromatograph (GC). Because p-chlorobenzoylchloride (PCBOC) has the same boiling point as PCBN but a slower reaction rate, the reaction was continued until all of the PCBOC had been consumed. In general, when less than 5 wt % of PCBTC remained (after 15 to 20 hours of reaction at 220° C.) the 1 L sublimate receiver was exchanged for a clean one and the product was up and over distilled. After cooling the reactor, it was recharged with the sublimate from the previous run, NH$_4$Cl, and PCBTC, and the sequence was repeated. In this manner, 7 kg of PCBTC gave a 90.5 wt % isolated yield of PCBN with an average purity of 97 wt % by GC area%.

EXAMPLES 2 TO 10

Example 1 was repeated using various starting materials ("Feed"), catalysts, and conditions. The following table summarizes these experiments. In the table, "OCBN" is orthochlorobenzonitrile, "HCMX" is hexachloro-m-xylene, and "IPN" is isophthalonitrile.

| Run | Feed | Catalyst | Temp. | Yield | Purity | Product |
|---|---|---|---|---|---|---|
| 1 | PCBTC | MgCl$_2$ | 220° C. | 85 | 97 | PCBN |
| 2 | " | MgO | " | 91 | 97 | " |
| 3 | " | MgSO$_4$ | " | 95 | — | " |
| 4 | " | CaO | " | 87 | — | " |
| 5 | " | CaCO3 | " | 98 | — | " |
| 6 | OCBTC | MgO | " | 90 | 98 | OCBN |
| 7 | DCBTC | MgCl$_2$ | 240° C. | 90 | 99 | DCBN |
| 8 | " | MgO | 230° C. | 95 | 99 | " |
| 9 | HCMX | MgO | 220° C. | 84 | — | IPN |

We claim:

1. A method of making an aromatic nitrile comprising reacting a benzotrichloride having the general formula

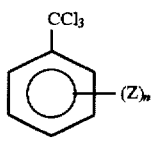

with 1 to 3 moles of a source of ammonia per mole of said benzotrichloride in the presence of about 0.01 to about 5 wt % of a catalyst having the general formula M$_{p/2}$O or MX$_p$·mH$_2$O and about 0.01 to about 5 wt % water, as free water or water of hydration, based on the weight of said benzotrichloride, where Z is R, X,

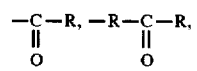

—ROR, or —OR, R is alkyl from C$_1$ to C$_{20}$ or aryl from C$_1$ to C$_{25}$, X is halogen, and M is beryllium, magnesium, calcium, strontium, or barium n is 0 to 5, m is 0 to 6, and p is the valence of M.

2. A method according to claim 1 wherein said benzotrichloride is parachlorobenzotrichloride.

3. A method according to claim 1 wherein said benzotrichloride is 3,4-dichlorobenzotrichloride.

4. A method according to claim 1 wherein said source of ammonia is ammonia.

5. A method according to claim 1 wherein said source of ammonia is ammonium chloride.

6. A method according to claim 1 wherein said M is magnesium.

7. A method according to claim 1 wherein m is 0.

8. A method according to claim 1 wherein the number of moles of said source of ammonia per mole of said benzotrichloride is about 1.05 to about 1.1.

9. A method according to claim 1 wherein the amount of said catalyst is about 0.1 to about 1 wt %, based on the weight of said benzotrichloride.

10. A method according to claim 1 wherein the amount of said water is about 0.1 to about 1 wt %, based on the weight of said benzotrichloride.

11. A method of making parachlorobenzonitrile comprising reacting parachlorobenzotrichloride at about 200° to about 220° C. with about 1.05 to about 1.1 moles per mole of said parachlorobenzotrichloride of an ammonium source selected from the group consisting of ammonia and ammonium chloride in the presence of about 0.1 to about 1.0 wt % of a catalyst selected from the group consisting of magnesium chloride and magnesium oxide and about 0.1% to about 1 wt % water, where said wt %'s are based on the weight of said parachlorobenzotrichloride.

12. A method according to claim 11 wherein said ammonia source is ammonia.

13. A method according to claim 11 wherein said ammonia source is ammonium chloride.

14. A method according to claim 11 wherein said catalyst is magnesium chloride.

15. A method according to claim 11 wherein said catalyst is magnesium oxide.

16. A method of making 3,4-dichlorobenzonitrile comprising reacting 3,4-dichlorobenzotrichloride at about 220° to about 240° C. with about 1.05 to about 1.1 moles per mole of said 3,4-dichlorobenzotrifluoride of an ammonium source selected from the group consisting of ammonia and ammonium chloride in the presence of about 0.1 to about 1.0 wt % of a catalyst selected from the group consisting of magnesium chloride and magnesium oxide and about 0.1% to about 1 wt % water, where said wt %'s are based on the weight of said 3,4-dichlorobenzotrichloride.

17. A method according to claim 16 wherein said ammonia source is ammonia.

18. A method according to claim 16 wherein said ammonia source is ammonium chloride.

19. A method according to claim 16 wherein said catalyst is magnesium chloride.

20. A method according to claim 16 wherein said catalyst is magnesium oxide.

* * * * *